United States Patent [19]

Blacklock

[11] Patent Number: 5,709,137
[45] Date of Patent: Jan. 20, 1998

[54] TORQUE CLUTCHED REVERSIBLE RATCHET WRENCH

[76] Inventor: Gordon D. Blacklock, 3321 Columbia NE., Albuquerque, N. Mex. 87107

[21] Appl. No.: 632,157

[22] Filed: Apr. 15, 1996

Related U.S. Application Data

[63] Continuation-in-part of Ser. No. 427,256, Apr. 24, 1995, Pat. No. 5,653,151.
[51] Int. Cl.$^6$ .................................................. B25B 23/14
[52] U.S. Cl. ............................................... 81/467; 81/60
[58] Field of Search ........................... 81/58.5, 60, 438, 81/439, 467, 125.1

[56] References Cited

U.S. PATENT DOCUMENTS

| | | | |
|---|---|---|---|
| 161,022 | 3/1875 | Freeman | 81/58.5 |
| 1,359,325 | 11/1920 | Butler | 81/58.5 X |
| 3,635,654 | 1/1972 | McFarland | |
| 4,056,020 | 11/1977 | Coviello | 81/438 |
| 4,273,173 | 6/1981 | Smith et al. | 81/438 |
| 4,276,791 | 7/1981 | Thompson | |
| 4,808,106 | 2/1989 | Foreman | 81/60 |

FOREIGN PATENT DOCUMENTS

| | | | |
|---|---|---|---|
| 670225 | 2/1929 | France | 81/58.5 |
| 603807 | 4/1960 | Italy | 81/58.5 |

OTHER PUBLICATIONS

Craftsman Mechanics' Tools, Aug. 30, 1955; p. 10, automotive wrenches from "F", Aug. 1930.

Primary Examiner—James G. Smith
Attorney, Agent, or Firm—Terrance L. Siemens

[57] ABSTRACT

A two sided or headed ratcheting driving wrench. Each side or head has a rotatable receptacle constrained to rotate in only one direction by interengaging teeth formed in the receptacle and in its housing. Both sets of teeth may be pointed or rounded. In one direction, torque locks the receptacle to the housing, and thus drives a tool such as a screw driver blade or a socket. In the other direction, torque causes the receptacle to disengage from the housing. Thus, conventional, intermittent one way rotation is assured. The receptacle and its surrounding chamber formed in each tool head are dimensioned and configured to assure engagement between receptacle and head when placed under torque in one direction. The wrench has a lever or handle which has a significant portion of its length offset from linear to allow for working in tight quarters. The receptacle has a square hole formed therein, for receiving a driven tool. The driven tool comprises a square block cooperating with the square hole of the receptacle, and has two oppositely oriented blades, sockets, or other tool elements. In another option, the square block is separate from the driven tool, to allow for versatility. In a further option, a fastener is formed integrally with the receptacle. Optionally, the drive system has provision for limiting torque acting on the driven fastener. Direction of operation is reversed by inverting the wrench. No adjustment of a lever is required.

22 Claims, 4 Drawing Sheets

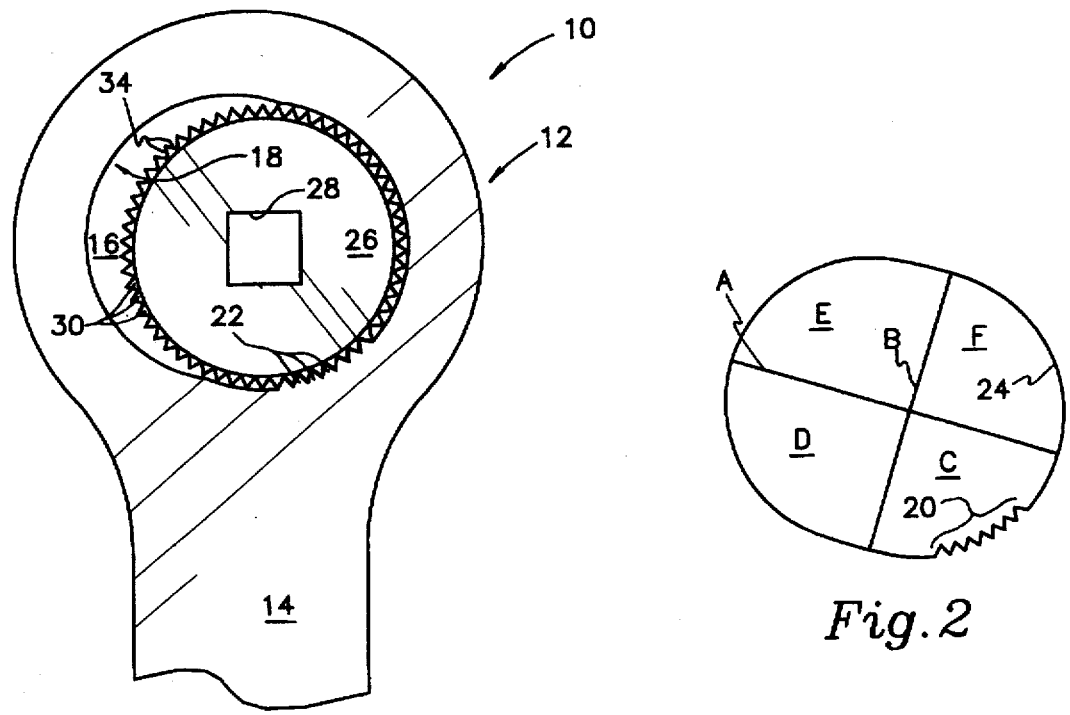
Fig. 1
Fig. 2
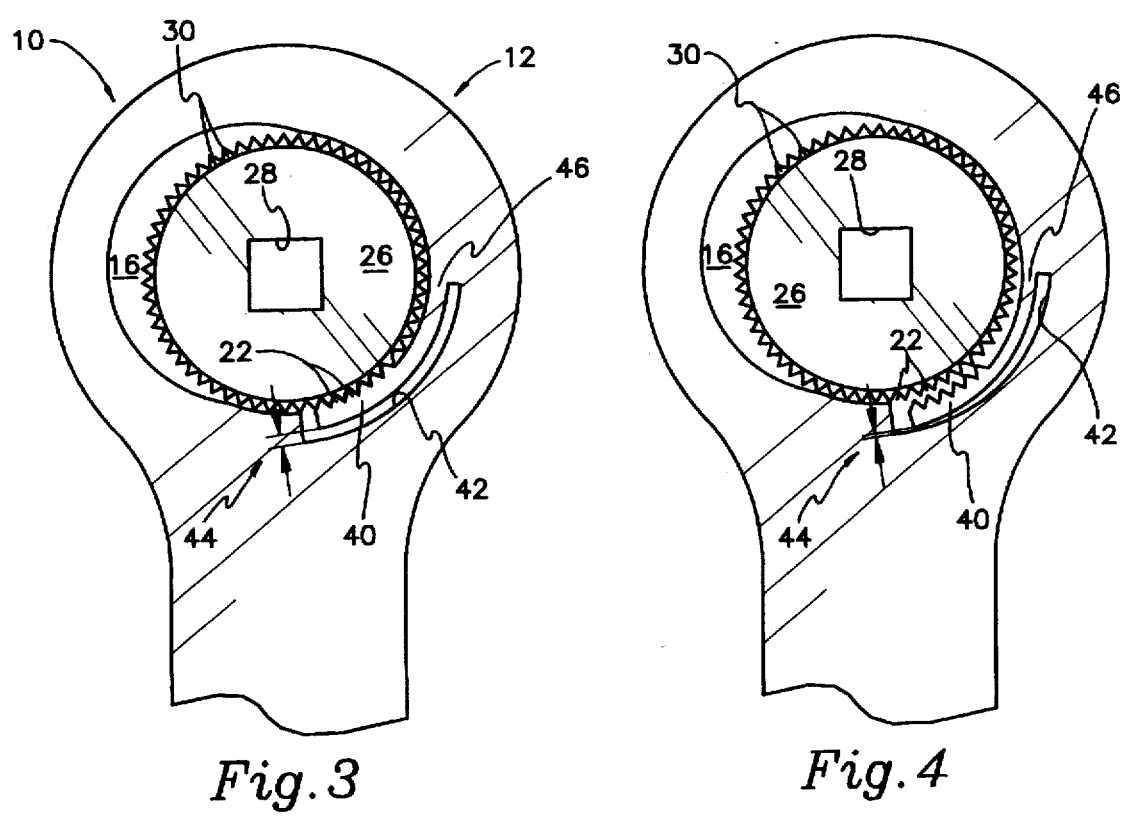
Fig. 3
Fig. 4

TORQUE CLUTCHED REVERSIBLE RATCHET WRENCH

REFERENCE TO RELATED APPLICATION

This application is a Continuation-In-Part of Ser. No. 08/427,256, filed Apr. 24, 1995 now U.S. Pat. No. 5,653,151.

BACKGROUND OF THE INVENTION

1. Field of the Invention

The present invention relates to a hand held wrench for enabling rotation of sockets, screw driver blades, and other hand tools. The wrench comprises a handle giving the user leverage, and a working head which is either directly usable with square or otherwise configured drives, screw driving blades, and the like, or which may have a receptacle for interchangeably accepting various tool driving shafts.

2. Description of the Prior Art

Reversible ratcheting wrenches have long been desired by service and assembly mechanics and technicians for installing and removing threaded fasteners. For the convenience of the technician, it is important that a wrench be quickly converted to include any desired driver, blade, socket, and so forth, since efficiency of assembly and disassembly is usually directly linked to the technician's compensation. For this reason, reversible wrenches have become quite popular.

A second desirable aspect is that a single driving tool accept interchangeable drivers, blades, sockets, and like accessories cooperating with the driver. These drivers, blades, sockets, and like accessories will be referred to hereinafter as tools. Interchangeability enables a single wrench to perform many tasks. The wrench can gain added capabilities as additional tools are made available. This arrangement has favorable economic repercussions, since each additional size or configuration requires a working element or tool of limited complexity and cost.

An additional desirable aspect is that the wrench have as few separate parts as possible. In traditional reversible ratcheting wrench driving tools, separate internal and external parts are required to adjust the direction of operation. However, it is possible to design the wrench so as to eliminate such intermediate components. An example is seen in U.S. Pat. No. 161,022, issued to George W. Freeman on Mar. 23, 1875. The Freeman wrench has a rotatable inner member occupying a generally round cavity formed in the head thereof. The inner member has external teeth which engage a single internal tooth formed in the cavity of the head of the wrench. Both internal and external teeth have one side oriented at a severe angle to a line tangential with the respective rounded shape of the inner member or of the round cavity of the head of the wrench, the other side oriented at a slight angle to the tangential line. This arrangement is typical of pawl and ratchet devices.

However, the internal geometry and structure of this wrench differ from those of the present invention, and the differences, although some aspects being so slight as not to be readily discernible upon casual inspection, lead to significantly different performance characteristics.

Careful examination of the Freeman wrench will reveal that the internal rotatable member is not surroundably constrained in the manner of the present invention. It is possible that the rotatable member in Freeman's device will rotate out of an engaged position with respect to the fixed encircling member of the tool after only a very limited degree of rotation in response to resistance to torque applied to the wrench. In the present invention, the encircling member is dimensioned and configured to avoid this occurrence.

A number of other prior art wrenches providing reversibility and plural driving features will be reviewed. U.S. Pat. No. 3,635,654, issued to Frederick R. McFarland on Jan. 18, 1972, illustrates a two headed driver having reversibly rotating heads. Each head has a socket of different dimensions, so that each head provides two sizes of nut driving sockets. The entire wrench will, therefore, provide four total different driving sockets. This tool is limited to the four sizes of sockets originally installed therein. Also, the tool is of complicated construction, requiring a number of internal springs and pawls.

A wrench having a removable socket is shown in U.S. Pat. No. 4,276,791, issued to John W. Thompson on Jul. 7, 1981. The wrench includes the usual bipositionable pawl, and has a lever and linkage for adjusting the driving direction. The present invention is unencumbered by such a pawl and linkage.

None of the above inventions and patents, taken either singly or in combination, is seen to describe the instant invention as claimed.

SUMMARY OF THE INVENTION

The present inventive wrench combines the advantages of uncomplicated construction with the features of reversibility and interchangeability of tool varieties. The wrench has an elongated handle, and a head at each end of the handle, for containing operative components.

Each head has a member which rotates unidirectionally by a ratchet. An inner member, or receptacle, is rotatably disposed within the head. The receptacle is rotated with ratchet action by the following arrangement. The head has an internal chamber of generally circular configuration. Part of the circular inner wall of the head is smooth, and part has inwardly oriented teeth. The receptacle has an external wall corresponding to the internal wall of the head. The receptacle wall also has a smooth section and a toothed section. The teeth are pitched in well known fashion to interengage receptacle and head when torque is applied in one direction, and to slip when torque is applied in the opposite direction.

The principles regarding ratcheting action described thus far are generally conventional. However, the novel wrench eliminates the need for actuating levers and internal parts conventionally required to achieve ratcheting action and operation in a reverse direction by virtue of its unique geometry. Rather than being truly circular, the internal chamber of the head is very slightly elongated. The inwardly facing teeth disposed on the walls of the chamber are located such that the receptacle occupying the chamber is prevented from rolling or migrating out of engagement with the teeth of the chamber wall when torque is applied in one direction. However, slippage occurs readily when torque is applied in the other direction. Thus, the novel wrench is clutched by torque applied to the driven device.

The receptacle is so named because it preferably has a square hole for receiving insertable tools incorporating cooperating drivers, such as a screw driver blade, sockets, and the like, and square or other drivers not incorporating tools. A plurality of insertable tools of different dimensional and configurational characteristics gives widely diverse interchangeability of purpose.

Reversibility requires that the driver or insertable tool be removed from one face of the head of wrench, and reinstalled in the opposite face. Although it would be possible to have a driver or tool project outwardly from both faces of the head of the wrench, projection from both faces is preferably avoided in order to maintain as low a profile as possible, for working in tight quarters.

The square hole may also drive a square headed fastener directly. In such an embodiment, the wrench either lacks a square or equivalent driver. Alternatively, a fastener may be provided which incorporates characteristics of the internal, rotatable receptacle of the wrench. In this embodiment, the wrench lacks a permanently retained receptacle.

Reversing is accomplished by inverting the wrench within the user's hand, so that the formerly idle face of the head of the wrench, which previously faced away from the work, now faces the work. A tool or driver is now removed from one face of the head, and is reinserted into the receptacle so that it again faces the work. However, having reversed the tool, the direction in which the receptacle slips and locks up is changed. Effort of switching hand position of the tool is approximately the same as engaging and moving an actuating lever by finger, as is commonly performed in prior art tools to change direction.

Some other practical novel aspects of the wrench include configuration of the lever or handle to include offset. In some applications, notably in the dental field, this configuration allows a dentist to work in close quarters in a person's mouth when turning a threaded component of an implant prosthesis. The wrench is two headed so that forward and reverse operation are enabled in both a right handed mode and in a left handed mode. This is again a useful feature in the dental arts, wherein a dentist may be required to perform work on both right and left sides of a patient's mouth in cramped quarters.

In an alternative embodiment, the wrench has a torque limiting feature. The portion of the chamber wall bearing internally directed teeth is formed on a spring arm. When torque exceeds a predetermined value, this arm yields and moves away from the receptacle. The receptacle then disengages from the teeth of the chamber wall, and is no longer subject to torque.

Accordingly, it is a principal object of the invention to provide a reversing, ratchet action driving tool for driving tools such as screw driver blades and sockets.

It is another object of the invention to allow for interchangeability of individual tool sizes and types.

It is a further object of the invention to eliminate complicated internal construction of the driver.

Yet another object of the invention is to limit the amount of torque which may be applied to a tool installed in the wrench.

It is an additional object of the invention to eliminate the requirement for a separate socket for at least one size of fastener head.

It is again an object of the invention to provide the wrench with offset to enable operating in tight quarters.

It is an object of the invention to maintain the back of the working head flush regardless of which direction of rotation is operative.

A further object of the invention is to provide matched pairs of wrench and fastener.

Still another object of the invention is to provide, selectively, pointed and rounded teeth.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 1 is a top plan view of the invention.

FIG. 2 is an exaggerated, diagrammatic detail view showing geometric relationships and characteristics of the invention.

FIG. 3 is a top plan view of an alternative embodiment of the invention incorporating a feature limiting maximum torque which may be applied.

FIG. 4 is similar to FIG. 3, but illustrates deflection under actual torque limitation.

FIG. 12 is an exploded, perspective view of an alternative embodiment of the invention wherein one component of the wrench is formed integrally with a fastener or workpiece.

Similar reference characters denote corresponding features consistently throughout the attached drawings.

DETAILED DESCRIPTION OF THE PREFERRED EMBODIMENTS

Figure 5:
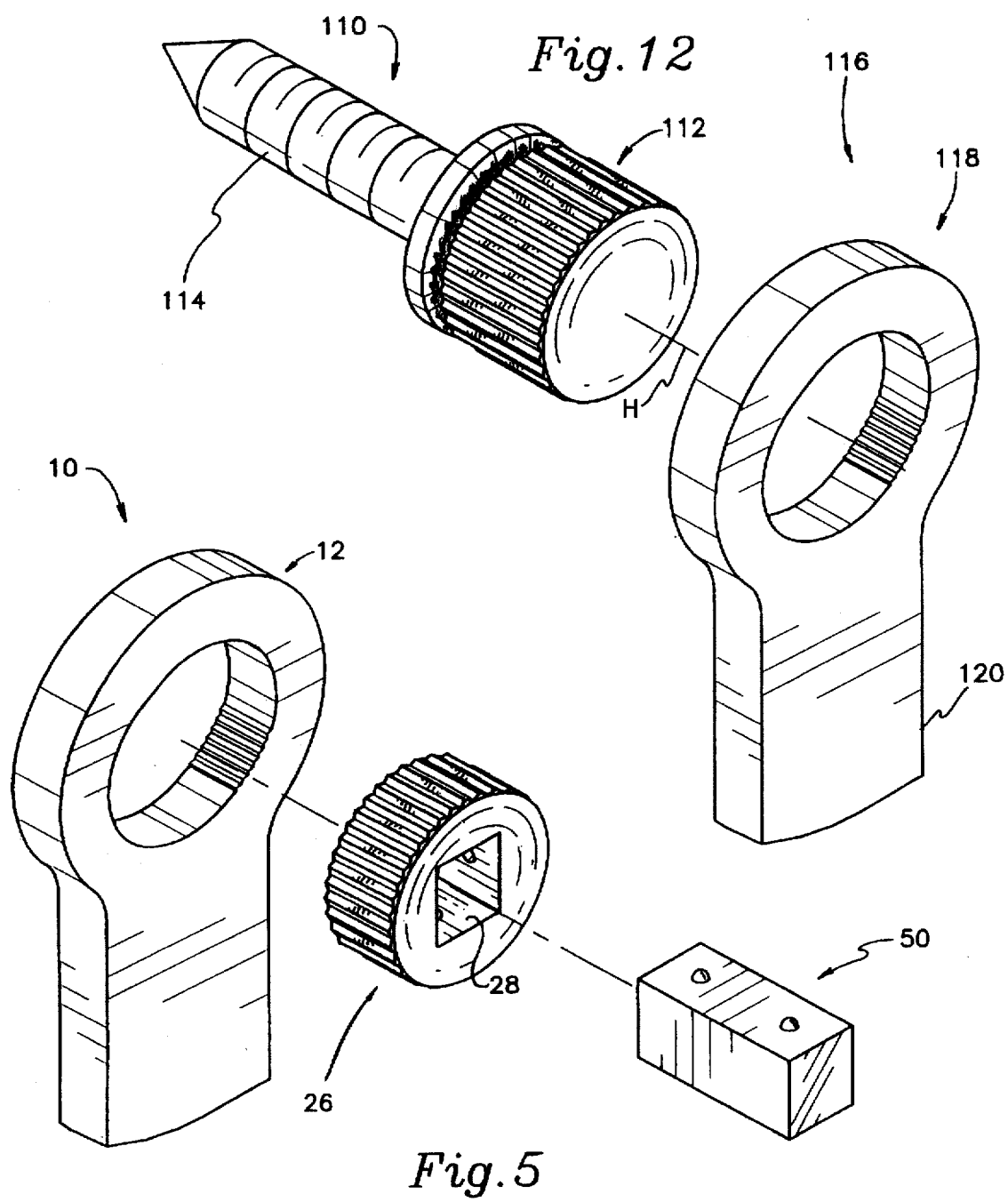
FIG. 5 is an exploded, perspective view of an optional feature of the invention providing a removable driving tool.

The novel reversible ratchet wrench 10 is seen in FIG. 1 to comprise a working head 12 having an elongated handle 14 defining therein a chamber 16 having a generally circular internal bounding surface 18. Handle 14 both provides ready grasp of wrench 10, and also enables leverage for applying a torque when tightening and loosening a driven element such as a tool (illustratively, such as tool 50 of FIG. 5). Handle 14 is shown truncated, and may be of any length suitable for the intended application.

For purposes of this discussion, driven elements will be referred to as tools. Tools will encompass any device which is insertable into or similarly engageable with the basic reversible ratchet wrench 10, and has structure for engaging wrench 10 and also has at least one working element. A working element is a screw driver blade, socket, square drive, hexagonal drive, or any other device for engaging a fastener or workpiece for the purpose of tightening and loosening the same, or for engaging a further working element which tightens or loosens a fastener or workpiece.

It is preferred that tool 10 be provided with a plurality of working inserts 12 having varying characteristics of dimension and configuration. A set of tools is thereby provided which requires but one driver and interchangeable working inserts to perform many tasks.

PRINCIPLE OF OPERATION

It must be noted that upon close inspection, chamber 16 is not truly circular. The overall configuration is slightly elongated, as will be explained further. Also, surface 18 comprises a first portion 20 (see FIG. 2) including inwardly directed teeth 22, and a second portion 24 (see FIG. 2) of smooth surface.

Still referring to FIG. 1, chamber 16 partially surrounds a driven receptacle 26, and where receptacle 26 is rotatably disposed within chamber 16. Receptacle 26 is so named since, in the preferred embodiment, it is characterized by a keyed opening 28 for receiving or engaging a tool or driver (both described hereinafter) for rotatably driving a tool. Opening 28 must be other than radially symmetrical, or round, so that the inserted tool or driver is effectively driven or rotated, and will not slip ineffectually within opening 28 when torque is applied to receptacle 26. Of course, the tool or driver inserted into opening 28 has a complementary or cooperating keyed member which fits closely within opening 28, so that it is retained by friction.

It is contemplated that in most applications, receptacle 26 will be retained within chamber 16 by provision of front and rear walls (not shown) preventing receptacle 26 from moving axially out of engagement with surface 18. Such walls may be formed integrally with working head 12, or may be formed separately and removably or permanently attached to working head 12.

Each externally directed tooth 30 and each internally directed tooth 22 is generally triangular and has two exposed intersecting faces 34 disposed at a pitch causing slippage between internal and external teeth 30, 22 when wrench 10 is rotated in one direction, and causing engagement between internal and external teeth 30, 22 when wrench 10 is rotated in the other direction. Of course, teeth 30, 22 are dimensioned and configured to interfittably cooperate with one another to enable engaged meshing.

FIG. 2 illustrates important geometry enabling wrench 10 to operate. Chamber 16, exaggerated in this view for clarity of understanding, is seen to have a major diameter A and a minor diameter B. Minor diameter B has a dimension of magnitude less than that of major diameter A. Thus, the overall configuration of Chamber 16 is oval when considered in the plan view of FIG. 2. Receptacle 26 (see FIG. 1) has a diameter of magnitude slightly less than that of minor diameter B in order to fit into chamber 16.

Major diameter A and minor diameter B intersect one another and effectively divide chamber 16 into quadrants C, D, E, F. First portion 20 of surface 18, that portion bearing teeth 22, is substantially disposed within any one quadrant C, D, E, or F. This enables engagement and disengagement of receptacle 26 responsive to a combination of applied torque and tooth pitch. When a fastener (illustratively, such as tool 50 of FIG. 5) encounters resistance, the effort of turning wrench 10 develops a torque acting on receptacle 26.

Given the relative position of portion 20 with respect to major and minor diameters A and B, in one direction of rotation, receptacle 26 is urged into effective engagement of teeth 22 because chamber 16 lacks sufficient diameter to allow receptacle 26 to roll or migrate out of engagement. In the other direction of rotation, chamber 16 provides sufficient clearance to allow receptacle 26 to back out of engagement with teeth 22. As wrench 10 is alternately rotated in opposing directions, ratcheting action ensues as receptacle 26 alternately engages teeth 22 and rotates in lockstep with working head 12, and disengages teeth 22 and remains in a constant position as working head 12 is rotated in a direction opposite that rotating receptacle 26 in lockstep with working head 12.

In summary, receptacle 26 selectively engages surface 24 and disengages therefrom. Receptacle 26 is constrained against disengagement by torque applied in one direction, and disengages responsive to torque applied in an opposite direction.

FEATURES OF THE INVENTION

Turning now to FIG. 3, an optional torque limiting feature of wrench 10 is explained. In the event that a driven tool (not shown) encounters resistance during tightening that would damage wrench 10, the tool, or a fastener (not shown), it is possible to protect these items by limiting torque applied to receptacle 26. In this embodiment, teeth 22 are supported or disposed upon an arm 40 anchored to working head 12.

Arm 40 is normally disposed at a first position, this being illustrated in FIG. 3, such that engagement of teeth 30 and teeth 22 is assured. As shown in FIG. 4, under great resistance, arm 40 deflects, withdrawing away from the center of chamber 16 into a second position. Teeth 30 and 22 thereby move out of mutual engagement. Close examination will reveal reduction of magnitude of gap 44 in FIG. 4, as constrasted to that of FIG. 3. This arrangement limits the maximum torque which may be applied to the driven device.

A spring biasing arm 40 into the first position is provided by virtue of the nature of the material from which working head 12 is fabricated. In this embodiment, working head 12 is fabricated from a material having a known degree of elasticity or resilience. A channel 42 is formed in working head 12. Channel 42 forms arm 40, and determines magnitude of a space or gap 44 separating arm 40 from surrounding working head 12. Monolithic or integral construction of working head 12 and arm 40 provides anchoring generally designated at 46.

It is an easy matter to determine appropriate thickness of arm 40 for predetermining appropriate force of elasticity or resiliency acting on arm 40, based upon characteristics of the material of working head 12. This calculation and dimensioning will result in deflection occurring at a predetermined amount of torque required to disengage receptacle 26 from working head 12.

Turning now to FIG. 5, a versatile driving arrangement is shown. Receptacle 26 has opening 28 which is preferably a square hole capable of accepting insertion of a square shank of a tool (not shown). However, it is preferable to provide a driving tool 50 comprising a complementary keyed member, in this example being square, which cooperatingly interfits within or engages opening 28.

Figure 6:
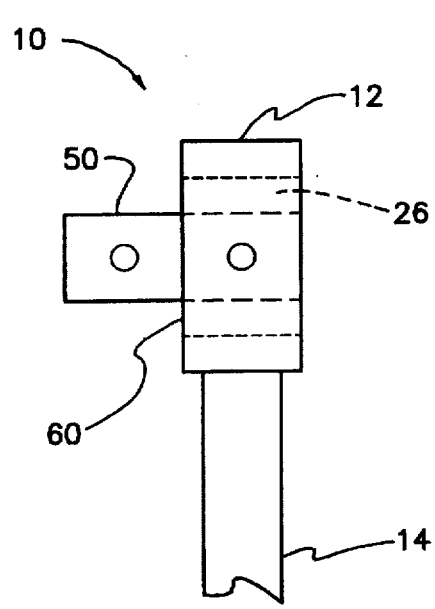
FIGS. 6 and 7 are similar side elevational views of the embodiment of FIG. 5, illustrating alternate positions of the removable driving tool.

With reference to FIG. 6, tool 50 is dimensioned and configured to project beyond receptacle 26 when installed therein. That portion of tool 50 which is exposed can in turn engage secondary tools (not shown). Secondary tools will be understood to encompass tools such as sockets, blades, and other tools having a female receptacle cooperatingly interfitting the exposed portion of tool 50.

Figure 7:
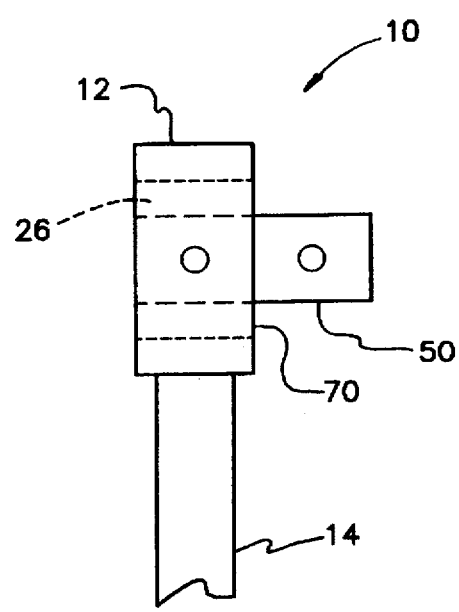

Comparing FIGS. 6 and 7, it will be seen that tool 50 can be moved to project from both sides of working head 12. This enables both clockwise and counterclockwise rotation of a tool, while simultaneously providing that the overall profile of wrench 10 is as compact as possible. This is important since the many uses of wrench 10 include many tasks which require working in tight or cramped quarters.

Figure 8:
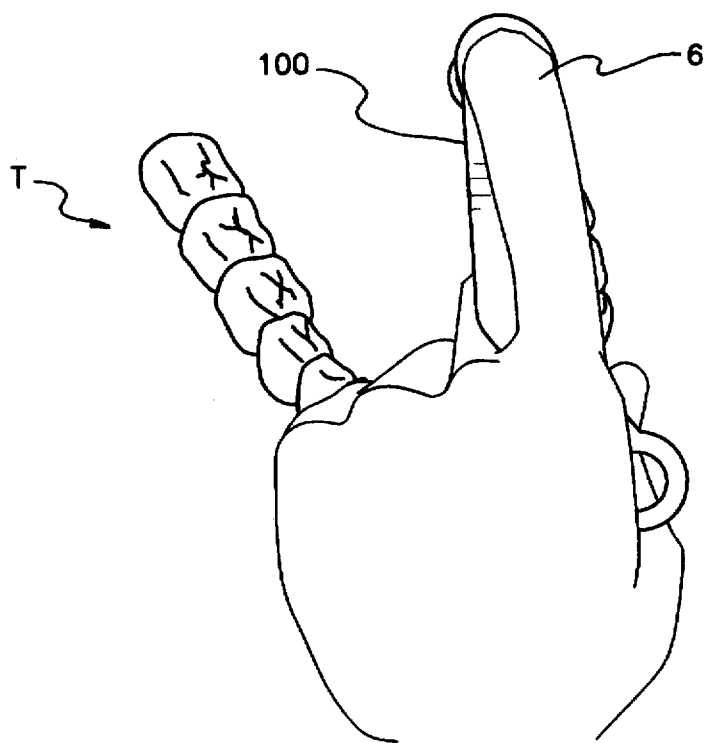
FIG. 8 is an environmental view of a preferred embodiment of the invention, illustrating a dental application of the novel wrench.

An example of such an application is illustrated in FIG. 8. A dentist installing a dental implant or prosthesis in a patient's teeth T may possibly be required to install and remove a healing cap or other threaded component of the implant. As illustrated in this view, the dentist must work from the outside of the mouth. With index finger G pressing downwardly on wrench 100 to ensure engagement of the tool blade (not shown) within a cooperating socket of the implant component (not shown), possible positions of the dentist's hand are limited.

Figure 9:
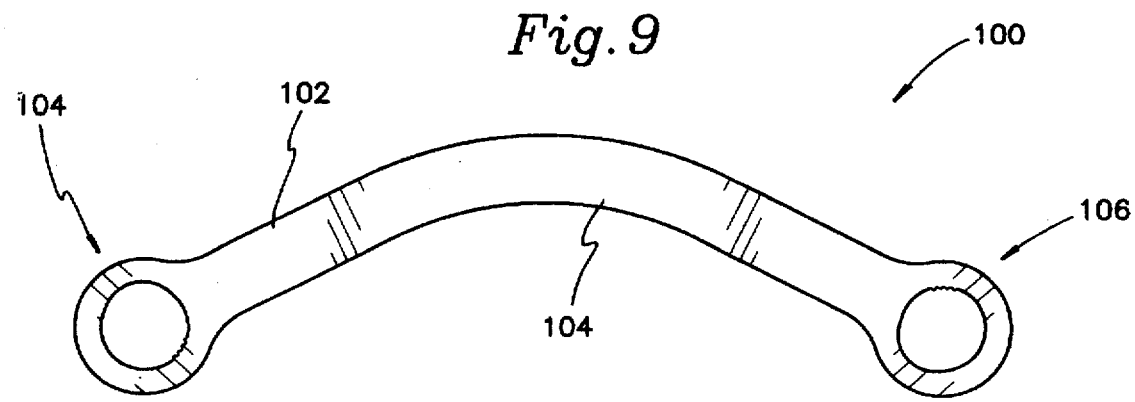
FIG. 9 is a top plan view of the preferred embodiment of FIG. 8, with a component omitted for clarity.

As seen in FIG. 9, wrench 100 incorporating the novel features described above has a handle 102 including a bend at 103. This bend causes handle 102 to provide unoccupied space for accommodating the dentist's hand, this situation being illustrated in FIG. 8.

A further feature of wrench 100 is illustrated in FIG. 9, wherein wrench 100 has two working heads 104, 106 located at opposite ends of handle 102. Both working heads 104, 106 have chambers and receptacles (omitted for clarity in this view) similar to those of the embodiment of FIG. 1, and configuration of the omitted elements are substantially similar to those shown in FIG. 1. The embodiment of FIG. 9 is particularly suited for dental work, wherein the bend at 104 enables both tightening and slackening of components to be performed in opposite hand fashion in dental work. Either head 104 or 106 may be selected, with a suitable tool (not shown) projecting from either one face 60 (see FIG. 6) or its opposed counterpart 70 (see FIG. 7). Therefore, maximal versatility and compactness are simultaneously achieved in wrench 100.

Figure 10:
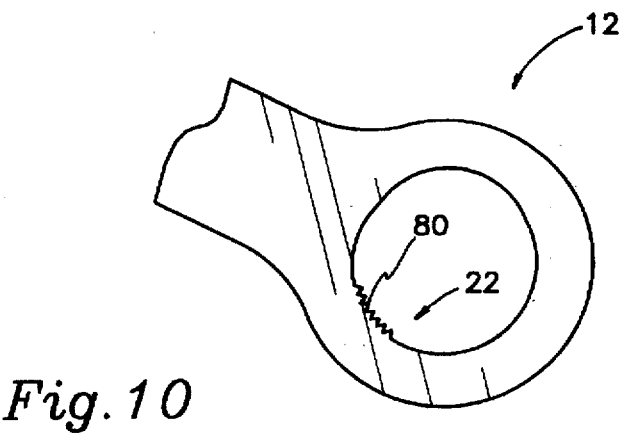

A further optional feature is described with reference to FIG. 10. It will be recalled from FIG. 1 that teeth 30 and teeth 22 are both formed to include intersecting faces 34. Throughout the drawing figures thus far described, such teeth intersect at a point, this being particularly pointed out at 80 in FIG. 10.

Figure 11:
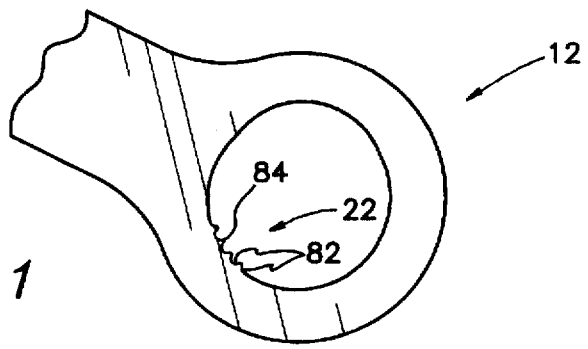
FIGS. 10 and 11 are top plan detail views of alternative forms of teeth, with a component omitted in each view for clarity.

Alternatively, as seen in FIG. 11, faces 82 may intersect at a curved corner 84. In this instance, teeth 22 are rounded. Although teeth 30 have been omitted from FIGS. 10 and 11 for clarity, it is to be understood that they are present in the invention. It will also be appreciated that teeth 30 and 22 are interchangeable since they must interfit. It is preferred that teeth 30 and 22 be similar in configuration, either both being pointed, as in FIG. 10, or both rounded, as in FIG. 11.

Turning now to FIG. 12, the invention may be practiced such that a fastener 110 incorporates features of receptacle 26 of FIG. 1. In the embodiment of FIG. 12, receptacle 112, which rotates about axis H of rotation when being turned, has a threaded shank 114 projecting coaxially from receptacle 112 with respect to axis H of rotation. In this embodiment, a threaded fastener 110 is provided which is readily driven by a ratchet wrench 116 incorporating the novel improvements set forth above. A supply of fasteners 110 may be employed with wrench 116, which comprises only working head 118 and handle 120. This arrangement expedites installation and removal of specialized or dedicated fasteners 110, while requiring a specialized or dedicated wrench 116 which readily enables ratcheting turning of fasteners 110.

It will be apparent that many variations and modifications to the invention are possible. For example, opening 28 of receptacle 26 may be other than square. Tools not thus far described may be employed with the novel wrench. Myriad further variations are possible.

Therefore, it is to be understood that the present invention is not limited to the embodiments described above, but encompasses any and all embodiments within the scope of the following claims.

I claim:

1. A reversible ratchet wrench for driving fasteners and interchangeable tools, comprising:

a first working head having an elongated handle and a chamber therein, said chamber having a generally circular internal surface having a first portion including internally directed teeth and a second portion of smooth surface, said generally circular internal surface having a major diameter dimension and a minor diameter dimension of magnitude less than that of said major diameter;

a driven receptacle rotatably disposed within said chamber, said receptacle having a generally circular external surface having externally directed teeth interfittably cooperating with said internally directed teeth of said working head, said receptacle further having apparatus for engaging a tool usable with said reversible ratchet wrench, each one of said externally directed teeth of said receptacle and said internally directed teeth of said working head having two exposed intersecting faces disposed at a pitch causing slippage when said reversible ratchet wrench is rotated in one direction and causing engagement when said reversible ratchet wrench is rotated in the other direction, said receptacle having a receptacle diameter dimension of magnitude slightly less than that of said minor diameter dimension of said circular internal surface of said chamber of said first working head, such that said externally directed teeth of said receptacle are constrained against moving out of engagement with said internally directed teeth of said first working head when said reversible ratchet wrench is rotated against a resistance in a first direction, a torque arising from the resistance and urging said receptacle into engagement with said working head, and said externally directed teeth of said receptacle are enabled to move out of engagement with said internally directed teeth of said working head when said reversible ratchet wrench is rotated in an opposite direction; and apparatus for limiting torque applied to said receptacle, comprising an arm anchored to said chamber of said working head, said arm supporting said internally directed teeth of said chamber, having apparatus for moving into a first position assuring engagement of said internally directed teeth of said chamber of said working head with said externally directed teeth of said receptacle and into a second position disengaging said internally directed teeth of said chamber of said working head from said externally directed teeth of said receptacle, and having a spring biasing said arm into said first position.

2. The reversible ratchet wrench according to claim 1, said major diameter dimension of said internal surface of said chamber and said minor diameter dimension of said internal surface of said chamber intersecting and dividing said chamber into four quadrants, said first portion of said chamber of said working head including said internally directed teeth being disposed substantially within one of said quadrants of said chamber, whereby said outwardly directed teeth of said receptacle engage said internally directed teeth of said internal surface of said chamber such that when said receptacle selectively engages said internal surface of said chamber, said receptacle is constrained against disengagement by torque applied in one direction, and said receptacle disengages from said internal surface of said chamber responsive to torque applied in an opposite direction.

3. The reversible ratchet wrench according to claim 1, said elongated handle having a bend therein, said bend causing said handle to provide unoccupied space for accommodating a user's hand, whereby said handle assists the user to work in cramped quarters.

4. The reversible ratchet wrench according to claim 1, further comprising a second working head and a second chamber therein, said second chamber disposed upon said elongated handle at an end opposite that bearing said first working head and having internal cross sectional configuration substantially similar to that of said chamber of said first working head.

5. The reversible ratchet wrench according to claim 1, said two faces of each one of said externally directed teeth of said receptacle and of each one of said internally directed teeth of said internal surface of said chamber of said first working head intersecting at a point, whereby said teeth are pointed.

6. The reversible ratchet wrench according to claim 1, said two faces of each one of said externally directed teeth of said receptacle and of each one of said internally directed teeth of said internal surface of said chamber of said first working head intersecting at a curved corner, whereby said teeth are rounded.

7. The reversible ratchet wrench according to claim 1, said apparatus for engaging a tool further comprising a keyed opening, whereby a tool having a complementary keyed member is insertable into said receptacle and is rotatably driven by said reversible ratchet wrench.

8. The reversible ratchet wrench according to claim 7, further comprising a driving tool having a complementary keyed member interfittably engaging said keyed opening of said receptacle, said keyed member being dimensioned and configured to project beyond said receptacle when installed therein, whereby said complementary keyed member is engageable with secondary tools.

9. A reversible ratchet wrench for driving interchangeable tools, comprising:

a first working head having an elongated handle and a chamber therein, said chamber having a generally circular internal surface having a first portion including internally directed teeth and a second portion of smooth surface, said generally circular internal surface having a major diameter dimension and a minor diameter dimension of magnitude less than that of said major diameter;

a driven receptacle rotatably disposed within said chamber, said receptacle having a generally circular external surface having externally directed teeth interfittably cooperating with said internally directed teeth of said working head, said receptacle further having apparatus for engaging a tool usable with said reversible ratchet wrench, each one of said externally directed teeth of said receptacle and said internally directed teeth of said working head having two exposed intersecting faces disposed at a pitch causing slippage when said reversible ratchet wrench is rotated in one direction and causing engagement when said reversible ratchet wrench is rotated in the other direction, said receptacle having a receptacle diameter dimension of magnitude slightly less than that of said minor diameter dimension of said circular internal surface of said chamber of said first working head, such that said externally directed teeth of said receptacle are constrained against moving out of engagement with said internally directed teeth of said first working head when said reversible ratchet wrench is rotated against a resistance in a first direction, a torque arising from the resistance and urging said receptacle into engagement with said working head, and said externally directed teeth of said receptacle are enabled to move out of engagement with said internally directed teeth of said working head when said reversible ratchet wrench is rotated in an opposite direction, said major diameter dimension of said internal surface of said chamber and said minor diameter dimension of said internal surface of said chamber intersecting and dividing said chamber into four quadrants, said first portion of said chamber of said working head including said internally directed teeth being disposed substantially within one of said quadrants of said chamber, whereby said outwardly directed teeth of said receptacle engage said internally directed teeth of said internal surface of said chamber such that when said receptacle selectively engages said internal surface of said chamber, said receptacle is constrained against disengagement by torque applied in one direction, and said receptacle disengages from said internal surface of said chamber responsive to torque applied in an opposite direction, and apparatus for limiting torque applied to said receptacle, comprising an arm anchored to said chamber of said working head, said arm supporting said internally directed teeth of said chamber, having apparatus for moving into a first position assuring engagement of said internally directed teeth of said chamber of said working head with said externally directed teeth of said receptacle and into a second position disengaging said internally directed teeth of said chamber of said working head from said externally directed teeth of said receptacle, and having a spring biasing said arm into said first position.

10. The reversible ratchet wrench according to claim 9, said apparatus for engaging a tool further comprising a keyed opening, whereby a tool having a complementary keyed member is insertable into said receptacle and is rotatably driven by said reversible ratchet wrench.

11. The reversible ratchet wrench according to claim 10, further comprising a driving tool having a complementary keyed member interfittably engaging said keyed opening of said receptacle, said keyed member being dimensioned and configured to project beyond said receptacle when installed therein, whereby said complementary keyed member is engageable with secondary tools.

12. A reversible ratchet wrench for driving interchangeable tools, comprising:

a first working head having an elongated handle and means defining a chamber within said first working head, said chamber having a concave, curved internal surface having a first quadrant portion including internally directed teeth and a second, adjacent quadrant portion of smooth surface, said internal surface having a minor diameter dimension;

a driven receptacle rotatably disposed within said chamber, said receptacle having a generally circular external surface having externally directed teeth interfittably cooperating with said internally directed teeth of said working head, said receptacle further having tool engaging apparatus for engaging a tool usable with said reversible ratchet wrench, each one of said externally directed teeth of said receptacle and said internally directed teeth of said working head being triangular and having two exposed intersecting faces disposed at a pitch causing slippage when said reversible ratchet wrench is rotated in one direction and causing engagement when said reversible ratchet wrench is rotated in the other direction, said receptacle having a receptacle diameter dimension of magnitude slightly less than that of said minor diameter dimension of said internal surface of said chamber of said first working head, such that said externally directed teeth of said receptacle are constrained against moving out of engagement with said internally directed teeth of said first working head when said reversible ratchet wrench is rotated against a resistance in a first direction, a torque arising from the resistance and urging said receptacle into engagement with said working head, and said externally directed teeth of said receptacle are enabled to move out of engagement with said internally directed teeth of said working head when said reversible ratchet wrench is rotated in an opposite direction, and contact is made between said receptacle and said second quadrant portion of said chamber when said externally directed teeth are disposed in driving contact with internally directed teeth of said working head, whereby said outwardly directed teeth of said receptacle engage said inwardly directed teeth of said internal surface of said chamber such that when said receptacle selectively engages said internal surface of said chamber, said receptacle is constrained against disengagement by torque applied in one direction, and said receptacle disengages from said internal surface of said chamber responsive to torque applied in an opposite direction.

13. The reversible ratchet wrench according to claim 12, said tool engaging apparatus of said receptacle further comprising a keyed opening, whereby a tool having a complementary keyed member is insertable into said receptacle and is rotatably driven by said reversible ratchet wrench.

14. The reversible ratchet wrench according to claim 13, further comprising a driving tool having a complementary keyed member interfittably engaging said keyed opening of said receptacle, said keyed member being dimensioned and configured to project beyond said receptacle when installed therein, whereby said complementary keyed member is engageable with secondary tools.

15. The reversible ratchet wrench according to claim 12, said elongated handle further having a bend therein, said bend causing said handle to provide unoccupied space for accommodating a user's hand, whereby said handle assists the user to work in cramped quarters.

16. The reversible ratchet wrench according to claim 12, further comprising a second working head having a second elongated handle and a second chamber therein, said second chamber having internal cross sectional configuration substantially similar to that of said chamber of said first working head.

17. A reversible ratchet wrench for driving fasteners and interchangeable tools, comprising:

a first working head having a chamber formed therein and an elongated handle, said chamber having a generally circular internal surface having a first portion including internally directed teeth and a second portion of smooth surface;

a driven receptacle rotatably disposed within said chamber, said receptacle having a generally circular external surface having externally directed teeth interfittably cooperating with said internally directed teeth of said working head, said receptacle further having apparatus for engaging a tool usable with said reversible ratchet wrench, each one of said externally directed teeth of said receptacle and said internally directed teeth of said working head having two exposed intersecting faces disposed at a pitch causing slippage when said reversible ratchet wrench is rotated in one direction and causing engagement when said reversible ratchet wrench is rotated in the other direction, said internal surface of said chamber of said first working head having a resiliently deflectable member, said internally directed teeth of first portion of said internal surface being disposed upon said resiliently deflectable member, whereby said externally directed teeth of said receptacle are constrained against moving out of engagement with said internally directed teeth of said first working head when said reversible ratchet wrench is rotated against a resistance in a first direction, a torque arising from the resistance and urging said receptacle into engagement with said working head, and said externally directed teeth of said receptacle are enabled to move out of engagement with said internally directed teeth of said working head when said reversible ratchet wrench is rotated in an opposite direction.

18. The reversible ratchet wrench according to claim 17, said elongated handle having a bend therein, said bend causing said handle to provide unoccupied space for accommodating a user's hand, whereby said handle assists the user to work in cramped quarters.

19. The reversible ratchet wrench according to claim 17, further comprising a second working head and a second chamber therein, said second chamber disposed upon said elongated handle at an end opposite that bearing said first working head and having a second driven receptacle rotatably disposed within said second chamber, whereby said reversible ratchet wrench has two working heads.

20. The reversible ratchet wrench according to claim 17, said two faces of each one of said externally directed teeth of said receptacle and of each one of said internally directed teeth of said internal surface of said chamber of said first working head intersecting at a point, whereby said teeth are pointed.

21. The reversible ratchet wrench according to claim 17, said two faces of each one of said externally directed teeth of said receptacle and of each one of said internally directed teeth of said internal surface of said chamber of said first working head intersecting at a curved corner, whereby said teeth are rounded.

22. The reversible ratchet wrench according to claim 17, said apparatus for engaging a tool further comprising a keyed opening, whereby a tool having a complementary keyed member is insertable into said receptacle and is rotatably driven by said reversible ratchet wrench.

* * * * *